United States Patent
Hijikata et al.

(10) Patent No.: US 9,861,717 B2
(45) Date of Patent: Jan. 9, 2018

(54) PET BOTTLE STERILIZATION APPARATUS AND STERILIZATION METHOD

(71) Applicants: SUNTORY HOLDINGS LIMITED, Osaka (JP); SUNTORY BEVERAGE & FOOD LIMITED, Tokyo (JP)

(72) Inventors: Shoichi Hijikata, Osaka (JP); Tokio Takahashi, Osaka (JP)

(73) Assignees: SUNTORY HOLDINGS LIMITED, Osaka (JP); SUNTORY BEVERAGE & FOOD LIMITED, Tokyo (JP)

( * ) Notice: Subject to any disclaimer, the term of this patent is extended or adjusted under 35 U.S.C. 154(b) by 323 days.

(21) Appl. No.: 14/382,134

(22) PCT Filed: Feb. 21, 2014

(86) PCT No.: PCT/JP2014/054992
§ 371 (c)(1),
(2) Date: Aug. 29, 2014

(87) PCT Pub. No.: WO2014/141894
PCT Pub. Date: Sep. 18, 2014

(65) Prior Publication Data
US 2016/0250367 A1    Sep. 1, 2016

(30) Foreign Application Priority Data

Mar. 11, 2013    (JP) .................... 2013-048433

(51) Int. Cl.
*A61L 2/00*    (2006.01)
*A61L 9/00*    (2006.01)
(Continued)

(52) U.S. Cl.
CPC .............. *A61L 2/208* (2013.01); *B65B 55/06* (2013.01); *B65B 55/08* (2013.01); *B65B 55/10* (2013.01);
(Continued)

(58) Field of Classification Search
CPC ... A61L 2/00; A61L 2/208; A61L 2/22; A61L 2/26; B67C 7/0073
(Continued)

(56) References Cited

U.S. PATENT DOCUMENTS 6,332,484 B1    12/2001    Stahlecker et al.
6,528,016 B1    3/2003    Kohler et al.
(Continued)

FOREIGN PATENT DOCUMENTS

DE    102004036063 A1    2/2006
EP    2008670 A1    12/2008
(Continued)

OTHER PUBLICATIONS

The English Translation of JP 2001-054556 (previously submitted on Jul. 27, 2016).*

(Continued)

*Primary Examiner* — Monzer R Chorbaji
(74) *Attorney, Agent, or Firm* — Greenblum & Bernstein, P.L.C.

(57) ABSTRACT

A PET bottle sterilization apparatus is for consecutively sterilizing multiple PET bottles (B) while conveying them, and includes a hydrogen peroxide introducing means (5) for introducing hydrogen peroxide into a PET bottle (B) so as to sterilize its interior and a hot air supplying means (6) for introducing hot air into the sterilized PET bottle (B) so as to eliminate hydrogen peroxide remaining inside it. This apparatus includes a plasma introducing means (P) for introducing plasma into a PET bottle (B) by injecting plasma through a nozzle at at least one time point among a time point before hydrogen peroxide is introduced into the PET bottle (B), a time point after hydrogen peroxide was introduced into the PET bottle (B) and furthermore before hot air is introduced into the PET bottle (B), and a time point after hot air was introduced into the PET bottle (B).

6 Claims, 4 Drawing Sheets

(51) Int. Cl.
  *B01J 19/08*    (2006.01)
  *B08B 6/00*    (2006.01)
  *B08B 7/00*    (2006.01)
  *A61L 2/20*    (2006.01)
  *B65B 55/10*    (2006.01)
  *B67C 7/00*    (2006.01)
  *B65B 55/06*    (2006.01)
  *B65B 55/08*    (2006.01)

(52) U.S. Cl.
  CPC ......... *B67C 7/0073* (2013.01); *A61L 2202/13* (2013.01)

(58) Field of Classification Search
  USPC ...... 422/1, 22, 28, 32, 186.05, 292; 134/1.1, 134/6
  See application file for complete search history.

(56)         References Cited

U.S. PATENT DOCUMENTS

| 8,323,582 B2 | 12/2012 | Ko et al. |
| 2004/0208781 A1 | 10/2004 | Hayashi et al. |
| 2006/0011262 A1 | 1/2006 | Stienen |
| 2008/0032059 A1 | 2/2008 | Zimmerer et al. |
| 2008/0107562 A1 | 5/2008 | Hayashi et al. |
| 2009/0317295 A1 | 12/2009 | Yonesu et al. |

FOREIGN PATENT DOCUMENTS

| JP | 2001-054556 | * | 2/2001 | ............... A61L 2/14 |
| JP | 2001-054556 | A | 2/2001 | |
| JP | 2001-145689 | A | 5/2001 | |
| JP | 2011-145689 | A | 5/2001 | |
| JP | 2004-357888 | A | 12/2004 | |
| JP | 2010-116212 | A | 5/2010 | |
| JP | 2010-518959 | A | 6/2010 | |
| JP | 2011-072809 | A | 4/2011 | |
| WO | 2008102993 | A1 | 8/2008 | |

OTHER PUBLICATIONS

Japanese Office Action issued with respect to application No. 2013-048433, dated Oct. 29, 2014.
International Search Report issued with respect to PCT/JP2014/054992, dated May 28, 2014.
Written Opinion of the International Searching Authority issued with respect to PCT/JP2014/054992, dated May 28, 2014.
Japanese Office Action issued for application No. 2013-048433, dated Apr. 9, 2015.

* cited by examiner

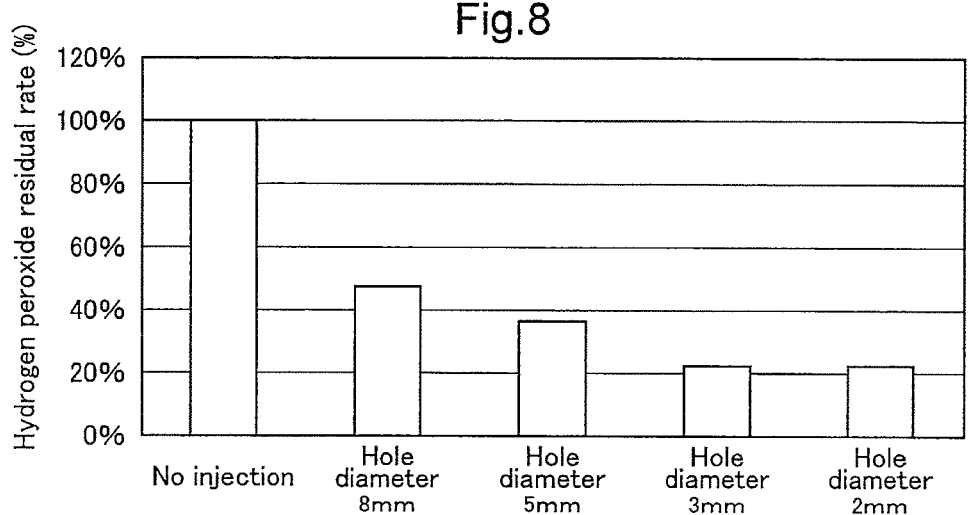
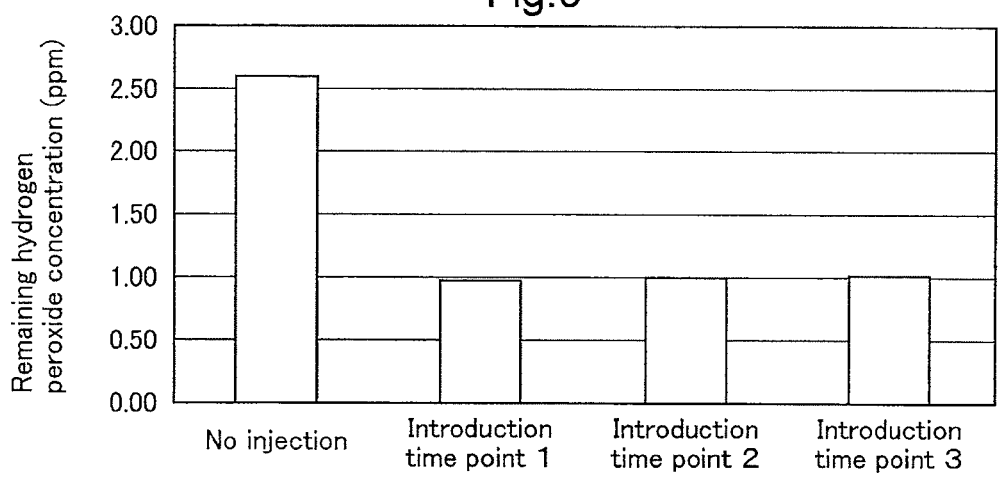
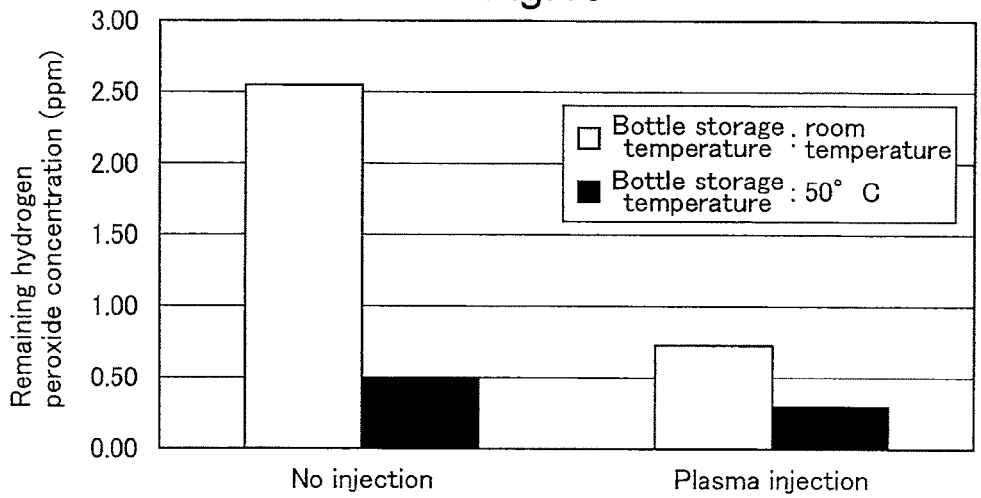

PET BOTTLE STERILIZATION APPARATUS AND STERILIZATION METHOD

TECHNICAL FIELD

The present invention relates to a sterilization apparatus and a sterilization method for application in a PET bottle aseptic filling system.

BACKGROUND ART

The apparatus disclosed in Patent Document 1 below is known as an example of a conventional sterilization apparatus applied in a PET bottle (bottle made of polyethylene terephthalate) aseptic filling system. The disclosed apparatus is configured such that hydrogen peroxide mist is introduced into a PET bottle to sterilize the interior faces of the PET bottle, hot air is then pumped into the PET bottle such that the hydrogen peroxide mist floating inside the PET bottle is discharged to the outside, and then aseptic warm water is introduced into the PET bottle to clean it.

CONVENTIONAL ART DOCUMENTS

Patent Documents

Patent Document 1: JP 2010-116212A (see FIG. 1 etc.)

DISCLOSURE OF THE INVENTION

Problem to be Solved by the Invention

Hydrogen peroxide readily adsorbs to PET bottles, and this is a main reason why hydrogen peroxide remains inside PET bottles after sterilization.

Conventional sterilization apparatuses use hot air and warm water to eliminate the remaining hydrogen peroxide, and the production of hot air and warm water has been costly, that is to say, the utility cost has been high. In view of this, it is conceivable to reduce the amount of hydrogen peroxide that is used in order to reduce the utility cost, but this results in lowering the effectiveness of sterilization, and it has not been possible to pursue a reduction in utility cost since it is not desirable to lower the effectiveness of sterilization in view of safety.

An object of the present invention is reduce the utility cost required when eliminating hydrogen peroxide that remains in a PET bottle, without requiring large-scale equipment and without reducing the amount of hydrogen peroxide that is used.

Means for Solving Problem

In a first characteristic configuration of a sterilization apparatus according to the present invention, a PET bottle sterilization apparatus is for consecutively sterilizing a plurality of PET bottles while conveying the PET bottles, and includes a hydrogen peroxide introducing means for introducing hydrogen peroxide into a PET bottle so as to sterilize the interior of the PET bottle and a hot air supplying means for introducing hot air into the sterilized PET bottle so as to eliminate hydrogen peroxide remaining inside the PET bottle, the PET bottle sterilization apparatus including: a plasma introducing means for introducing plasma into a PET bottle by injecting plasma through a nozzle at at least one time point among a time point that is before hydrogen peroxide is introduced into the PET bottle, a time point that is after hydrogen peroxide was introduced into the PET bottle and furthermore is before hot air is introduced into the PET bottle, and a time point that is after hot air was introduced into the PET bottle.

Operation and Effect

Plasma has a characteristic of decomposing hydrogen peroxide into water and oxygen.

For this reason, if plasma is introduced into a PET bottle by the plasma introducing means at a time point that is after hydrogen peroxide was introduced into the PET bottle, that is to say at a time point that is after hydrogen peroxide was introduced into the PET bottle and furthermore is before hot air is introduced into the PET bottle, and a time point that is after hot air was introduced into the PET bottle as in the above configuration, hydrogen peroxide remaining inside the PET bottle is decomposed and eliminated by the plasma, and moreover the hydrogen peroxide can be efficiently eliminated in a short time.

Also, when plasma is introduced into the PET bottle, the thermal energy of the plasma is transferred to the PET bottle, thus making it possible to heat the entire PET bottle in a short time.

When the PET bottle is heated, hydrogen peroxide is less likely to adsorb to it. For this reason, if plasma is introduced into the PET bottle by the plasma introducing means at a time point that is before hydrogen peroxide is introduced into the PET bottle as in the above configuration, the entirety of the PET bottle is heated in a short time, and therefore even if hydrogen peroxide is subsequently introduced into the PET bottle, the hydrogen peroxide is likely to float inside the PET bottle without adsorbing to the inner faces of the PET bottle. When hot air is then introduced into the PET bottle by the hot air supplying means, more of the hydrogen peroxide floating inside the PET bottle can be eliminated by being discharged in a short time.

Accordingly, if plasma is introduced at at least one time point among a time point that is before hydrogen peroxide is introduced into the PET bottle, a time point that is after hydrogen peroxide was introduced into the PET bottle and furthermore is before hot air is introduced into the PET bottle, and a time point that is after hot air was introduced into the PET bottle, hydrogen peroxide remaining inside the PET bottle can be efficiently eliminated in a short time. This enables reducing the amount of hot air and warm water that needs to be used when eliminating hydrogen peroxide that remains inside the PET bottle, and enables reducing utility cost overall. Also, introducing plasma enables hydrogen peroxide remaining inside the PET bottle to be efficiently eliminated in a short time, thus reducing the scale of the equipment necessary for eliminating hydrogen peroxide.

In a second characteristic configuration, the plasma introducing means includes a plurality of the nozzles, and the plurality of nozzles are arranged along a PET bottle conveyance path.

Operation and Effect

According to the above configuration, multiple nozzles are arranged along a PET bottle conveyance path, and therefore plasma can be introduced into multiple PET bottles at a time. As a result, remaining hydrogen peroxide can be efficiently eliminated from a greater number of PET bottles, thus improving the processing capability of the sterilization apparatus overall.

In a third characteristic configuration, the nozzle of the plasma introducing means is configured so as to inject plasma while following a PET bottle being conveyed.

Operation and Effect

According to the above configuration, plasma is injected while following a PET bottle being conveyed, thus making it possible to reliably introduce plasma into the PET bottle. Furthermore, since plasma can be injected in a conventional PET bottle conveying process, there is no need to introduce additional equipment, and the installation space can be substantially the same size as that for a conventional sterilization apparatus that does not inject plasma.

In a characteristic configuration of a sterilization method according to the present invention, a PET bottle sterilization method uses the sterilization apparatus according to any of the first to third characteristic configurations, wherein at least one of the inner diameter of the nozzle and the injection pressure of the plasma is adjusted according to the size of the PET bottle, and plasma is blown into the PET bottle so as to eliminate hydrogen peroxide remaining inside the PET bottle.

Operation and Effect

If at least one of the inner diameter of the nozzle and the injection pressure of the plasma is adjusted according to the size of the PET bottle, and plasma is blown into the PET bottle so as to eliminate hydrogen peroxide remaining inside the PET bottle as in the above configuration, plasma can be efficiently used with less waste and shortage, and it is possible to reduce utility cost for the sterilization apparatus overall.

In a characteristic configuration of a sterilization method according to the present invention, a PET bottle sterilization method is for consecutively sterilizing a plurality of PET bottles while conveying the PET bottles, and includes a hydrogen peroxide introducing step of introducing hydrogen peroxide into a PET bottle so as to sterilize the interior of the PET bottle and a hot air supplying step of introducing hot air into the sterilized PET bottle so as to eliminate hydrogen peroxide remaining inside the PET bottle, the PET bottle sterilization method including: a plasma introducing step of introducing plasma into a PET bottle by injecting plasma through a nozzle at at least one time point among a time point that is before hydrogen peroxide is introduced into the PET bottle, a time point that is after hydrogen peroxide was introduced into the PET bottle and furthermore is before hot air is introduced into the PET bottle, and a time point that is after hot air was introduced into the PET bottle.

Operation and Effect

Plasma has a characteristic of decomposing hydrogen peroxide into water and oxygen.

For this reason, if plasma is introduced into a PET bottle at a time point that is after hydrogen peroxide was introduced into the PET bottle, that is to say at a time point that is after hydrogen peroxide was introduced into the PET bottle and furthermore is before hot air is introduced into the PET bottle, and a time point that is after hot air was introduced into the PET bottle as in the above configuration, hydrogen peroxide remaining inside the PET bottle is decomposed and eliminated by the plasma, and moreover the hydrogen peroxide can be efficiently eliminated in a short time.

Also, when plasma is introduced into the PET bottle, the thermal energy of the plasma is transferred to the PET bottle, thus making it possible to heat the entire PET bottle in a short time.

When the PET bottle is heated, hydrogen peroxide is less likely to adsorb to it. For this reason, if plasma is introduced into the PET bottle at a time point that is before hydrogen peroxide is introduced into the PET bottle as in the above configuration, the entirety of the PET bottle is heated in a short time, and therefore even if hydrogen peroxide is subsequently introduced into the PET bottle, the hydrogen peroxide is likely to float inside the PET bottle without adsorbing to the inner faces of the PET bottle. When hot air is then introduced into the PET bottle in the hot air supplying step, more of the hydrogen peroxide floating inside the PET bottle can be eliminated by being discharged in a short time.

Accordingly, if plasma is introduced at at least one time point among a time point that is before hydrogen peroxide is introduced into the PET bottle, a time point that is after hydrogen peroxide was introduced into the PET bottle and furthermore is before hot air is introduced into the PET bottle, and a time point that is after hot air was introduced into the PET bottle, hydrogen peroxide remaining inside the PET bottle can be efficiently eliminated in a short time. This enables reducing the amount of hot air and warm water that needs to be used when eliminating hydrogen peroxide that remains inside the PET bottle, and enables reducing utility cost overall. Also, introducing plasma enables hydrogen peroxide remaining inside the PET bottle to be efficiently eliminated in a short time, thus reducing the scale of the equipment necessary for eliminating hydrogen peroxide.

BRIEF DESCRIPTION OF THE DRAWINGS

FIG. 8 is a diagram showing results of examining the shape of a nozzle for injecting plasma.

FIG. 9 is a diagram showing results of examining the plasma introduction time point.

FIG. 10 is a diagram showing results of examining the influence of the PET bottle storage temperature.

BEST MODE FOR CARRYING OUT THE INVENTION

Embodiment

Figure 1:
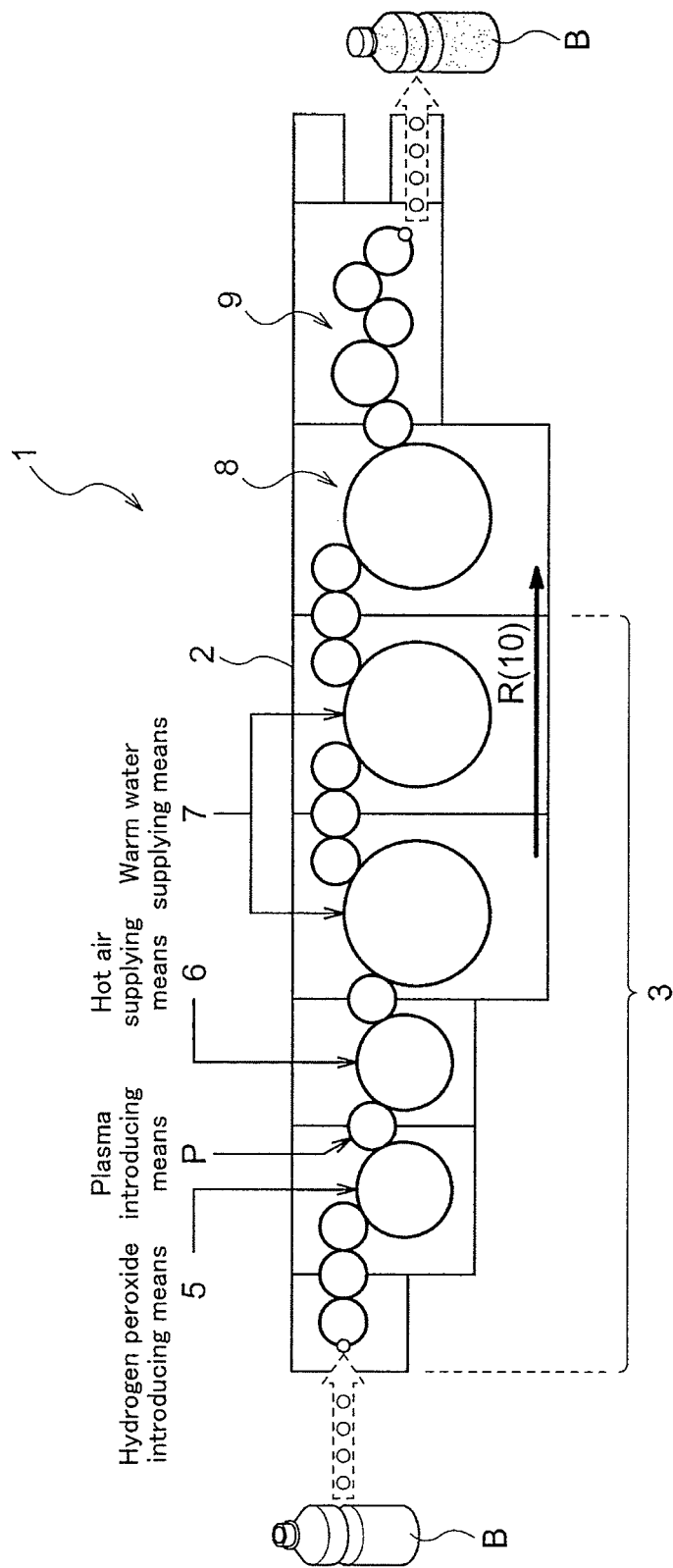
FIG. 1 is a diagram showing an overview of an aseptic filling system that includes a sterilization apparatus of the present invention.

The following describes a sterilization apparatus of the present invention in the case of being applied to an aseptic filling system for aseptic filling a PET bottle with a beverage at room temperature Aseptic Filling System As shown in FIG. 1, an aseptic filling system 1 is configured so as to include an aseptic chamber 2, a sterilization apparatus 3 for sterilizing a PET bottle B, a filling apparatus 8 for filling the PET bottle B with a sterilized beverage, a lid fastening apparatus 9 for fastening a lid of the PET bottle B filled with the beverage, and a conveying apparatus 10 for conveying the PET bottle B.

The interior of the aseptic chamber 2 has been subjected to predetermined sterilization, and is constantly supplied with aseptic air filtered by a filter so as keep the interior at a positive pressure (above atmospheric pressure).

The conveying apparatus 10 includes a conventionally-known turntable and star wheel, and forms a conveyance path R for PET bottles B.

The conveyance path R for PET bottles B is arranged inside the aseptic chamber 2, and the sterilization apparatus 3, the filling apparatus 8, and the lid fastening apparatus 9 arranged along the conveyance path R in the stated order beginning from the upstream side.

Note that excluding the sterilization apparatus 3 of the present invention, members including conventionally-known configurations can be used as the aseptic chamber 2, the filling apparatus 8, the lid fastening apparatus 9, and the conveying apparatus 10, and the operating conditions of these apparatus may also be set as necessary.

Sterilization Apparatus

The sterilization apparatus 3 of the present invention includes a hydrogen peroxide introducing means 5 that introduces hydrogen peroxide into the PET bottle B to sterilize the interior of the PET bottle B, a plasma introducing means P that injects plasma from a nozzle to introduce plasma into the PET bottle B, a hot air supplying means 6 that introduces hot air into the sterilized PET bottle B to eliminate hydrogen peroxide remaining inside the PET bottle B, and a warm water supplying means 7 that introduces aseptic warm water into the PET bottle B to clean it.

In the present embodiment, the hydrogen peroxide introducing means 5, the plasma introducing means P, the hot air supplying means 6, and the warm water supplying means 7 are arranged along the conveyance path R for PET bottles B in the stated order beginning on the upstream side, but the plasma introducing means P is not limited to this arrangement, and the plasma introducing means P may be provided between the hot air supplying means 6 and the warm water supplying means 7. When plasma is introduced into the PET bottle B by the plasma introducing means P, hydrogen peroxide remaining inside the PET bottle B is decomposed and eliminated by the plasma, thus making it possible to efficiently eliminate the hydrogen peroxide.

Also, when plasma is introduced into the PET bottle B, the thermal energy of the plasma is transferred to the PET bottle B, thus making it possible to heat the entire PET bottle B in a short time.

When the PET bottle B is heated, hydrogen peroxide is less likely to adsorb to it. For this reason, if plasma is introduced into the PET bottle B by the plasma introducing means P at a time point that is before hydrogen peroxide is introduced into the PET bottle B, the entirety of the PET bottle B is heated in a short time, and therefore even if hydrogen peroxide is subsequently introduced into the PET bottle B, the hydrogen peroxide is likely to float inside the PET bottle B without adsorbing to the inner faces of the PET bottle B. When hot air is then introduced into the PET bottle B by the hot air supplying means 6, more of the hydrogen peroxide floating inside the PET bottle B can be eliminated by being discharged in a short time.

Accordingly, the plasma introducing means P may be configured so as to be provided at at least one location among before the hydrogen peroxide introducing means 5, between the hydrogen peroxide introducing means 5 and the hot air supplying means 6, and between the hot air supplying means 6 and the warm water supplying means 7.

Figure 2:
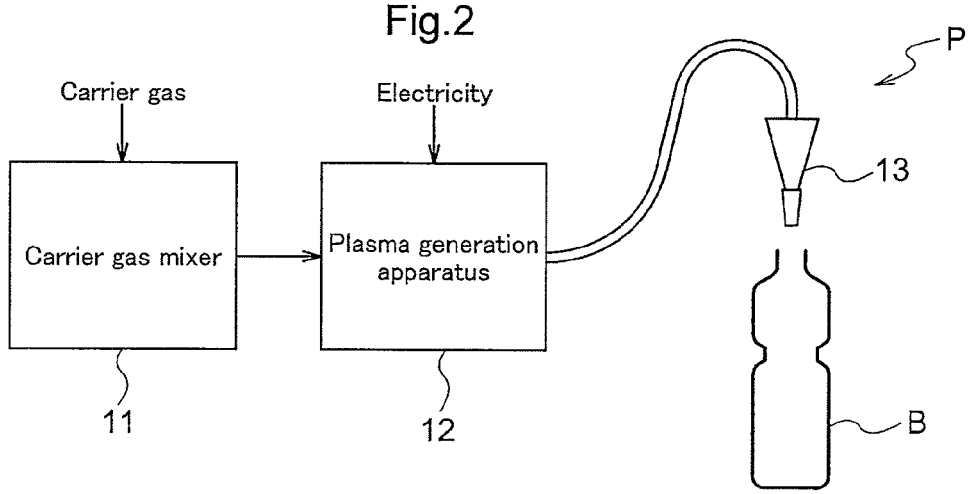
FIG. 2 is a diagram showing an overview of a plasma introducing means.

As shown in FIG. 2, the plasma introducing means P includes a carrier gas mixer 11 for mixing and adjusting the flow rate of a carrier gas, a plasma generation apparatus 12, and a nozzle 13 for injecting plasma, and the nozzle 13 is configured so as to be inserted into the opening of the PET bottle B and introduce plasma in that state. Note that a plasma injection hole is formed in the tip portion of the nozzle 13, and the tip portion is configured so as to be removable. This makes it possible to prepare multiple tip portions having different plasma injection hole diameters, and use the tip portions differently according to the situation by exchanging one for another whose plasma injection hole has an appropriate diameter, for example.

The plasma generation apparatus 12 may be a known apparatus that includes a control panel, a plasma control apparatus, a capacitor, and the like (not shown), and it is particularly preferable to use a high-frequency plasma generation apparatus (e.g., the high-frequency atmospheric pressure plasma surface treating apparatus PHW-1500 made by Wedge Co., Ltd.).

The nozzle 13 for injecting plasma can be a fixed nozzle that is fixed at a predetermined location, a following-type nozzle configured so as to inject plasma while following the conveyed PET bottles B, or a combination of the fixed nozzle and the following-type nozzle. Also, when using a fixed nozzle in particular, multiple fixed nozzles may be arranged and fixed in a line along the conveyance path R for PET bottles B.

There are no particular limitations on the shape of the nozzle 13. Also, the diameter of the plasma injection hole of the nozzle 13 may be appropriately selected according to the size of the PET bottle B, and in the case of a PET bottle B with a capacity of 500 mL for example, the diameter of the plasma injection hole is desirably 2 mm to 8 mm, and particularly preferably 2 mm to 3 mm.

The hydrogen peroxide introducing means 5 may be a known hydrogen peroxide injection apparatus that includes a hydrogen peroxide supply source and a nozzle that can spray hydrogen peroxide (not shown), this apparatus being configured such that the nozzle is inserted into the opening of the PET bottle B and introduces hydrogen peroxide into the PET bottle B in this state.

The hot air supplying means 6 may be a known hot air injection apparatus that includes a hot air supply source (not shown) and a nozzle (not shown) for injecting hot air, the apparatus being configured such that the nozzle is inserted into the opening of the PET bottle B and introduces hot air into the PET bottle B in this state.

The warm water supplying means 7 may be a known warm water injection apparatus that includes a warm water supply source (not shown) and a nozzle (not shown) for injecting warm water, the apparatus being configured such that the nozzle is inserted into the opening of the PET bottle B and introduces warm water into the PET bottle B in this state. Note that the warm water supplying means 7 does not necessarily need to be provided if hydrogen peroxide can be sufficiently eliminated by the plasma introducing means P and the hot air supplying means 6.

Room-Temperature Aseptic Filling Method

Next, a room-temperature aseptic filling method performed by the aseptic filling system 1 will be described. In this room-temperature aseptic filling method, a PET bottle B sterilizing step performed by the sterilization apparatus 3, a filling step performed by the filling apparatus 8, and a sealing step performed by the lid fastening apparatus 9 are carried out in the stated order in an aseptic environment at room temperature.

1. Sterilizing Step

Figure 3:
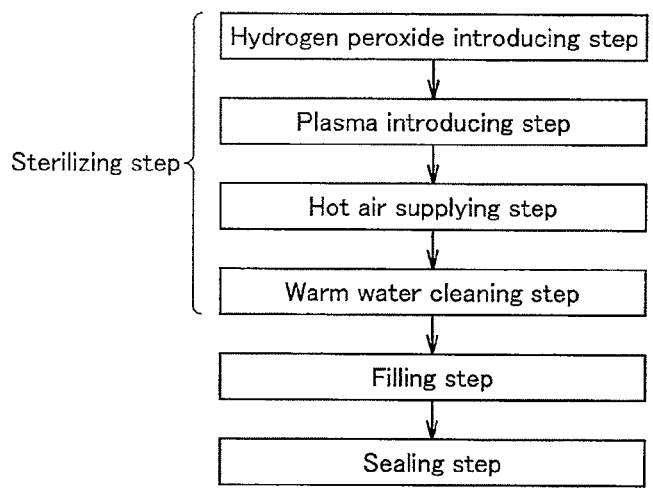
FIG. 3 is a diagram showing a flow of steps in an aseptic filling system that includes a sterilization method of the present invention.

As shown in FIG. 3, the sterilizing step is a step in which a hydrogen peroxide introducing step performed by the hydrogen peroxide introducing means 5, a plasma introducing step performed by the plasma introducing means P, a hot air supplying step performed by the hot air supplying means 6, and a warm water cleaning step performed by the warm water supplying means 7 are carried out in the stated order.

First, in the hydrogen peroxide introducing step, a nozzle is inserted into the opening of a PET bottle B that has been conveyed into the aseptic chamber 2, and an aqueous solution of hydrogen peroxide is sprayed into the PET bottle B. This sterilizes the interior of the PET bottle B. Note that the concentration, spray amount, and spray time for the aqueous solution of hydrogen peroxide here may be appropriately adjusted according to the size of the PET bottle B.

Next, in the plasma introducing step, a nozzle is inserted into the opening of the PET bottle B that was sterilized by the introduction of hydrogen peroxide, and plasma is injected into the PET bottle B.

The plasma output and injection time here may be appropriately adjusted according to the size of the PET bottle B, and in the case of a PET bottle B with a 500 mL capacity for example, it is desirable to set the plasma output of the plasma in the range of 500 W to 1,500 W, and set the plasma injection time in the range of 0.5 seconds to 3.0 seconds. According to this condition, it is possible to prevent plasma from burning the vicinity of the opening of the PET bottle B, without impairing the effect of decomposing the hydrogen peroxide.

Also, the type of plasma carrier gas may be normal compressed air obtained by an air compressor, nitrogen gas ($N_2$), a mixed gas of nitrogen ($N_2$) and argon (Ar), a mixed gas of nitrogen ($N_2$) and helium (He), or the like, but there is no particular limitation to these gases. In the case of using a mixed gas of nitrogen ($N_2$) and argon (Ar), the gas mixture ratio of the mixed gas is desirably 90% to 95% nitrogen ($N_2$) and 5% to 10% argon (Ar) for example, but there is no limitation to this ratio. In the case of using a mixed gas of nitrogen ($N_2$) and helium (He), this ratio is desirably 90% to 95% nitrogen ($N_2$) and 5% to 10% helium (He) for example, but there is no limitation to this ratio.

The gas pressure of the carrier gas (plasma injection pressure) may be appropriately adjusted according to the size of the PET bottle B, and in the case of a PET bottle B with a 500 mL capacity for example, it is desirable to set this gas pressure to 5 kgf to 10 kgf. If the gas pressure is set in this range, the plasma reaches the bottom face of the PET bottle B so as to be present in the entirety of the interior of the PET bottle B.

Due to the plasma introducing step, at least some of the hydrogen peroxide remaining inside the PET bottle is efficiently decomposed and eliminated by the plasma.

Next, in the hot air supplying step, a nozzle is inserted into the opening of the PET bottle B into which plasma was introduced, and hot air is injected into the PET bottle B. Accordingly, even if remaining hydrogen peroxide is floating inside the PET bottle B, that hydrogen peroxide is eliminated by being discharged. In the hot air supplying step in the present embodiment, more of hydrogen peroxide is eliminated by being discharged in a short time, thus making it possible to set the hot air temperature and air volume lower than in conventional technology. Note that the temperature, flow rate, and injection time of the hot air may be appropriately adjusted according to the size of the PET bottle B.

Next, in the warm water cleaning step, the PET bottle B into which hot air was supplied is vertically inverted, a nozzle is inserted into the opening of the PET bottle B from below, and aseptic warm water is injected into the PET bottle B as cleaning water. Accordingly, even if hydrogen peroxide has attached to inner faces of the PET bottle B, that hydrogen peroxide is eliminated by being washed away. Since almost of the hydrogen peroxide has already been eliminated, the amount of warm water need to wash away the hydrogen peroxide in the warm water cleaning step of the present embodiment can be set lower than in conventional technology. Note that the temperature, flow rate, and injection time of the warm water here may be appropriately adjusted according to the size of the PET bottle B.

Although the plasma introducing step is carried out after the hydrogen peroxide introducing step in the present embodiment, there is no limitation to this configuration. In other words, a configuration is possible in which, as described above, the plasma introducing means P is provided at at least one location among before the hydrogen peroxide introducing means 5, between the hydrogen peroxide introducing means 5 and the hot air supplying means 6, and between the hot air supplying means 6 and the warm water supplying means 7, and therefore the plasma introducing step is carried out at at least one time point among before the hydrogen peroxide introducing step, between the hydrogen peroxide introducing step and the hot air supplying step, and between the hot air supplying step and the warm water cleaning step.

2. Filling Step

In the filling step, the PET bottle B that underwent the sterilizing step is again vertically inverted, and the PET bottle B is filled with a beverage that has been subjected to predetermined sterilization in advance.

3. Sealing Step

In the sealing step, a lid that has undergone sterilization processing in advance is fastened to the opening of the PET bottle B that underwent the filling step so as to seal the PET bottle B.

According to the above steps, molded PET bottles B are consecutively fed into the aseptic chamber 2 of the aseptic filling system 1, subjected to the sterilizing step by the sterilization apparatus 3, the beverage filling step by the filling apparatus 8, and the sealing step by the lid fastening apparatus 9 in the stated order while being conveyed along the conveyance path R, and then conveyed out of the aseptic chamber 2.

Working Examples

Various conditions were examined in the sterilization apparatus of the present invention. Note that hydrogen peroxide having a higher concentration than hydrogen peroxide actually used in sterilization apparatuses was used in order to check the effect of decomposing hydrogen peroxide with plasma and optimum plasma injection conditions in these working examples.

Examination of Plasma Output Condition

A predetermined amount of hydrogen peroxide was introduced into PET bottles with a 500 mL capacity, plasma was injected at various plasma outputs in the range of 500 W to 1,000 W, and the concentration of hydrogen peroxide remaining inside the PET bottles immediately after the plasma injection was measured.

Figure 4:
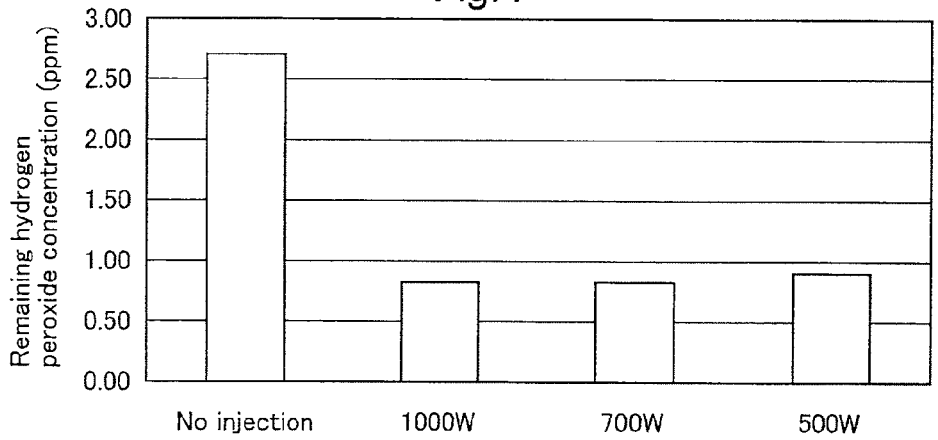
FIG. 4 is a diagram showing results of examining the plasma output condition.

As shown in FIG. 4, approximately 60% of the hydrogen peroxide was decomposed in the range of 500 W to 1,000 W.

Examination of Plasma Injection Time

A predetermined amount of hydrogen peroxide was introduced into PET bottles with a 500 mL capacity, plasma was injected for various plasma injection times in the range of 0.5 seconds to 2.0 seconds, the concentration of hydrogen peroxide remaining inside the PET bottles immediately after the plasma injection was measured, and the residual rate (%)

of hydrogen peroxide was calculated. Note that following-type nozzles and fixed nozzles were used.

Figure 5:
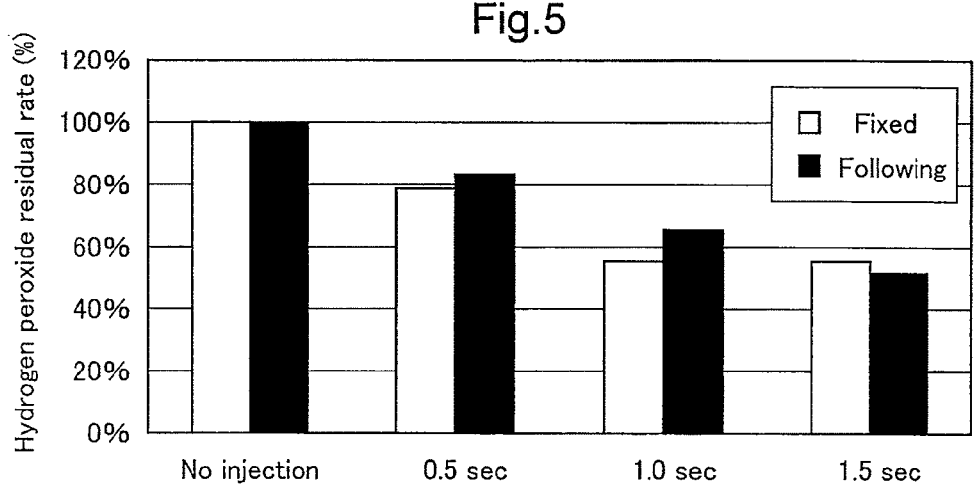
FIG. 5 is a diagram showing results of examining the plasma injection time.

As shown in FIG. 5, in both the case of using following-type nozzles and the case of using fixed nozzles, the longer the injection time was, the further the decomposition of hydrogen peroxide progressed, and the lower the residual rate decreased. Also, there was no particular difference in the effect of decomposing hydrogen peroxide between the following-type nozzles and the fixed nozzles, and it was demonstrated that the effect of decomposing hydrogen peroxide was approximately the same with both of the types of nozzles.

Examination of Plasma Carrier Gas

A predetermined amount of hydrogen peroxide was introduced into PET bottles with a 500 mL capacity, plasma was injected with various types of carrier gases, and the concentration of hydrogen peroxide remaining inside the PET bottles immediately after the plasma injection was measured.

The carrier gases that were prepared were air (normal compressed air obtained by an air compressor), nitrogen gas on its own, a mixed gas 1 (90% nitrogen gas, 10% argon gas), a mixed gas 2 (95% nitrogen gas, 5% argon gas), a mixed gas 3 (90% nitrogen gas, 10% helium gas), and a mixed gas 4 (95% nitrogen gas, 5% helium gas).

Figure 6:
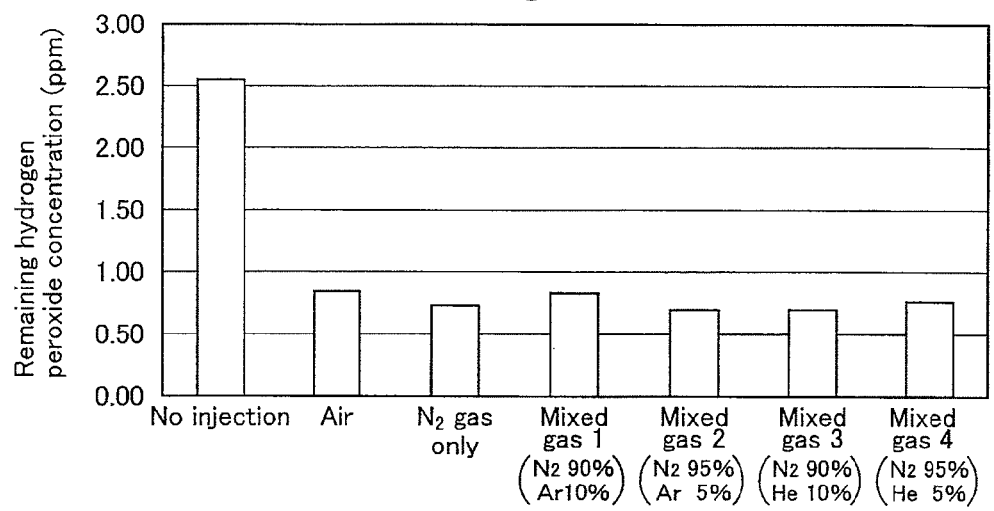
FIG. 6 is a diagram showing results of examining the plasma carrier gas.

As shown in FIG. 6, these six types of gases all had an effect of decomposing hydrogen peroxide and were able to be used as the carrier gas. Also, no big difference in particular was seen in the effect of decomposing hydrogen peroxide between these six types of gases.

Examination of Gas Pressure of Plasma Carrier Gas

A predetermined amount of hydrogen peroxide was introduced into PET bottles with a 500 mL capacity, plasma was injected at various carrier gas pressures in the range of 5.0 kgf to 9.7 kgf, and the concentration of hydrogen peroxide remaining inside the PET bottles immediately after the plasma injection was measured.

Figure 7:
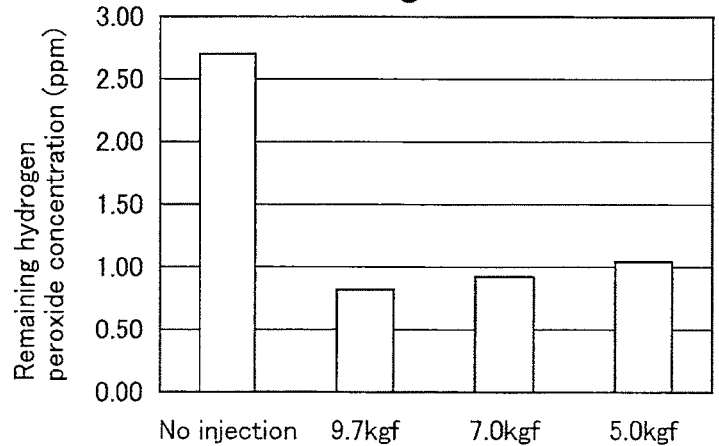
FIG. 7 is a diagram showing results of examining the gas pressure of the plasma carrier gas.

As shown in FIG. 7, a trend was observed in which the higher the gas pressure is, the greater the effect of decomposing hydrogen peroxide is. This is thought to be due to the fact that the higher the gas pressure is, the more likely the plasma is to reach the bottom face of the PET bottle so as to be present in the entirety of the interior of the PET bottle.

Examination of Shape of Plasma Injection Nozzle

A predetermined amount of hydrogen peroxide was introduced into PET bottles with a 500 mL capacity, plasma was injected using four types of nozzles having different plasma injection hole diameters, and the concentration of hydrogen peroxide remaining inside the PET bottles immediately after the plasma injection was measured. Note that the diameters of the plasma injection holes of the nozzles were 2 mm, 3 mm, 5 mm, and 8 mm respectively.

As shown in FIG. 8, a trend was observed in which the smaller the plasma injection hole diameter is, the greater the effect of decomposing hydrogen peroxide is, and it was thought that a nozzle having a plasma injection hole diameter of 2 mm to 3 mm is desirable for a PET bottle with a 500 mL capacity.

Examination of Plasma Introduction Time Point

PET bottles with a 500 mL capacity were used, the plasma introducing step was carried out at three time points, namely between the hydrogen peroxide introducing step and the hot air supplying step (time point 1), between the hot air supplying step and the warm water cleaning step (time point 2), and before the hydrogen peroxide introducing step (time point 3), and the concentration of hydrogen peroxide remaining inside the PET bottles immediately after the plasma injection was measured.

As shown in FIG. 9, approximately 60% of the hydrogen peroxide was decomposed at all of the time points, and there was almost no difference in the effect of decomposing hydrogen peroxide.

Examination of Influence of PET Bottle Storage Temperature

Two PET bottles with a 500 mL capacity were stored at room temperature and 50° C. respectively, a predetermined amount of hydrogen peroxide was introduced into the PET bottles, plasma was injected, and the concentration of hydrogen peroxide remaining inside the PET bottles immediately after the plasma injection was measured.

As shown in FIG. 10, even when plasma was not introduced, the residual rate of hydrogen peroxide was lower in the PET bottle stored at 50° C. than in the PET bottle stored at room temperature. This therefore suggested that the higher the temperature condition applied to the PET bottle is before the PET bottle is introduced into the aseptic filling system 1, the less likely hydrogen peroxide is to be adsorbed. A PET bottle heating method in which plasma is introduced into PET bottles using the plasma introducing means P is most favorable as a means for heating the PET bottles before the PET bottles are introduced into the aseptic filling system 1, but there is no limitation to this, and another heating means may be used as long as it is possible to heat the PET bottles without causing any deformation, damage, or the like.

Other Embodiments

In the above-described embodiment, a step for pre-heating the PET bottle may be provided before the sterilizing step as necessary.

INDUSTRIAL APPLICABILITY

The sterilization apparatus and the sterilization method of the present invention can be favorably applied in a room-temperature aseptic filling system for beverages in particular.

DESCRIPTION OF REFERENCE SIGNS

1 Aseptic filling system
9 Aseptic chamber
3 Sterilization apparatus
5 Hydrogen peroxide introducing means
6 Hot air supplying means
7 Warm water supplying means
8 Filling apparatus
9 Lid fastening apparatus
10 Conveying apparatus
11 Carrier gas mixer
12 Plasma generation apparatus
13 Nozzle
R Conveyance path
B PET bottle
P Plasma introducing means

The invention claimed is:

1. A PET bottle sterilization apparatus for consecutively sterilizing a plurality of PET bottles while conveying the PET bottles, comprising:
a hydrogen peroxide injector for introducing hydrogen peroxide into a PET bottle so as to sterilize the interior of the PET bottle and a hot air injector for introducing hot air into the sterilized PET bottle so as to eliminate hydrogen peroxide remaining inside the PET bottle, the PET bottle sterilization apparatus comprising:

at least one plasma injection nozzle for introducing plasma with air or nitrogen or both into a PET bottle by injecting plasma in a carrier gas consisting of at least one of air and nitrogen into the PET bottle at at least one time point among a time point that is before hydrogen peroxide is introduced into the PET bottle, and a time point that is after hot air was introduced into the PET bottle.

2. The PET bottle sterilization apparatus according to claim 1, wherein the at least one plasma injection nozzle comprises a plurality of nozzles arranged along a PET bottle conveyance path.

3. The PET bottle sterilization apparatus according to claim 1, wherein the at least one plasma injection nozzle is configured so as to inject plasma while following a PET bottle being conveyed.

4. A PET bottle sterilization method using a sterilization apparatus that is for consecutively sterilizing a plurality of PET bottles while conveying the PET bottles, comprising:

a hydrogen peroxide injector for introducing hydrogen peroxide into a PET bottle so as to sterilize the interior of the PET bottle and a hot air injector for introducing hot air into the sterilized PET bottle so as to eliminate hydrogen peroxide remaining inside the PET bottle, the PET bottle sterilization apparatus comprising:

at least one plasma injection nozzle for introducing plasma with air or nitrogen or both into a PET bottle by injecting plasma in a carrier gas consisting of at least one of air and nitrogen into the PET bottle at at least one time point among a time point that is before hydrogen peroxide is introduced into the PET bottle, and a time point that is after hot air was introduced into the PET bottle, the PET bottle sterilization method comprising:

adjusting at least one of the inner diameter of the nozzle and the injection pressure of the plasma according to the size of the PET bottle, and blowing plasma into the PET bottle so as to eliminate hydrogen peroxide remaining inside the PET bottle.

5. A PET bottle sterilization method using a sterilization apparatus that is for consecutively sterilizing a plurality of PET bottles while conveying the PET bottles, comprising:

a hydrogen peroxide injector for introducing hydrogen peroxide into a PET bottle so as to sterilize the interior of the PET bottle and a hot air injector for introducing hot air into the sterilized PET bottle so as to eliminate hydrogen peroxide remaining inside the PET bottle, the PET bottle sterilization apparatus comprising:

at least one nozzle for introducing plasma with air or nitrogen or both into a PET bottle by injecting plasma in a carrier gas consisting of at least one of air and nitrogen into the PET bottle at at least one time point among a time point that is before hydrogen peroxide is introduced into the PET bottle, and a time point that is after hot air was introduced into the PET bottle, the at least one nozzle comprising a plurality of nozzles, and the plurality of nozzles are arranged along a PET bottle conveyance path, the PET bottle sterilization method comprising:

adjusting at least one of the inner diameter of the nozzle and the injection pressure of the plasma according to the size of the PET bottle, and blowing plasma into the PET bottle so as to eliminate hydrogen peroxide remaining inside the PET bottle.

6. A PET bottle sterilization method using a sterilization apparatus for consecutively sterilizing a plurality of PET bottles while conveying the PET bottles, comprising:

a hydrogen peroxide injector for introducing hydrogen peroxide into a PET bottle so as to sterilize the interior of the PET bottle and a hot air supplying means for introducing hot air into the sterilized PET bottle so as to eliminate hydrogen peroxide remaining inside the PET bottle, the PET bottle sterilization apparatus comprising:

at least one nozzle for introducing plasma with air or nitrogen or both into a PET bottle by injecting plasma in a carrier gas consisting of at least one of air and nitrogen into the PET bottle at at least one time point among a time point that is before hydrogen peroxide is introduced into the PET bottle, and a time point that is after hot air was introduced into the PET bottle, the at one least nozzle being configured so as to inject plasma while following a PET bottle being conveyed, the PET bottle sterilization method comprising:

adjusting at least one of the inner diameter of the nozzle and the injection pressure of the plasma according to the size of the PET bottle, and blowing plasma into the PET bottle so as to eliminate hydrogen peroxide remaining inside the PET bottle.

* * * * *